US012582811B2

(12) United States Patent
Burkholz et al.

(10) Patent No.: US 12,582,811 B2
(45) Date of Patent: Mar. 24, 2026

(54) INSTRUMENT DELIVERY DEVICE WITH NESTED HOUSING

(71) Applicant: Becton, Dickinson and Company, Franklin Lakes, NJ (US)

(72) Inventors: Jonathan Karl Burkholz, Salt Lake City, UT (US); Megan S. Scherich, Salt Lake City, UT (US); Curtis H. Blanchard, Herriman, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 778 days.

(21) Appl. No.: 17/901,005

(22) Filed: Sep. 1, 2022

(65) Prior Publication Data

US 2024/0075270 A1     Mar. 7, 2024

(51) Int. Cl.
*A61M 39/02*          (2006.01)
(52) U.S. Cl.
CPC . *A61M 39/0247* (2013.01); *A61M 2039/0258* (2013.01); *A61M 2039/027* (2013.01);
(Continued)
(58) Field of Classification Search
CPC ...... A61M 39/0247; A61M 2039/0258; A61M 2039/027; A61M 2039/0273; A61M 2205/0222; A61M 2205/6081; A61M 25/0102; A61M 25/0113; A61M 25/0133; A61M 25/09041; A61M 25/0606
See application file for complete search history.

(56) References Cited

U.S. PATENT DOCUMENTS 5,549,576 A * 8/1996 Patterson .......... A61M 25/0662
                                                    604/247
11,389,624 B2   7/2022 Cook
(Continued)

FOREIGN PATENT DOCUMENTS

WO      2021236530 A1   11/2021
WO      2022032242 A1    2/2022

OTHER PUBLICATIONS

U.S. Appl. No. 63/273,226, Becton, Dickinson and Company, filed Oct. 29, 2021.
(Continued)

*Primary Examiner* — Theodore J Stigell
(74) *Attorney, Agent, or Firm* — The Webb Law Firm

(57)                ABSTRACT

Provided herein is an instrument delivery device for advancing an instrument into a vascular access device. The instrument delivery device includes an outer housing, a connector coupled to the outer housing and including a projection member that mates with the vascular access device, and an inner housing having a distal end positioned within the outer housing and engaged with a proximal end of the instrument. The inner housing moves relative to the outer housing so that a distal movement thereof moves the instrument from a first position to a second position, with a distal end of the instrument moving from within the outer housing to out beyond the distal end of the outer housing and the projection member. A fluid flow preventing seal provided in or adjacent the connector prevents a transfer of fluid between the vascular access device and the inner volume of the outer housing.

7 Claims, 6 Drawing Sheets

(52) U.S. Cl.
CPC ............... *A61M 2039/0273* (2013.01); *A61M 2205/0222* (2013.01); *A61M 2205/6081* (2013.01)

(56) References Cited

U.S. PATENT DOCUMENTS

| | | | |
|---|---|---|---|
| 2020/0016374 A1* | 1/2020 | Burkholz | ........... A61M 25/0113 |
| 2021/0213268 A1 | 7/2021 | Scherich et al. | |
| 2021/0290905 A1 | 9/2021 | Harding et al. | |
| 2021/0402152 A1 | 12/2021 | Burkholz et al. | |
| 2022/0218252 A1 | 7/2022 | Blanchard et al. | |
| 2022/0218955 A1* | 7/2022 | Scherich | ......... A61M 25/09041 |
| 2022/0218956 A1 | 7/2022 | Harding et al. | |

OTHER PUBLICATIONS

Utility U.S. Appl. No. 17/570,554, Becton, Dickinson and Company, filed Jan. 7, 2022.
Utility U.S. Appl. No. 17/709,935, Becton, Dickinson and Company, filed Mar. 31, 2022.
Utility U.S. Appl. No. 17/852,538, Becton, Dickinson and Company, filed Jun. 29, 2022.

* cited by examiner

INSTRUMENT DELIVERY DEVICE WITH NESTED HOUSING

BACKGROUND OF THE INVENTION

Field of the Invention

The present disclosure relates generally to instrument delivery devices for use with intravenous (IV) catheters and, more specifically, to instrument delivery devices for improving performance in terms of accessing the vasculature.

Description of Related Art

Vascular access devices (VADs) are used in the medical field to access peripheral vasculature of a patient for purposes of infusion therapy and/or blood withdrawal. Common types of VADs include over-the-needle peripheral intravenous catheters (PIVCs), peripherally inserted central catheters (PICCs), central venous catheters (CVCs), and midline catheters. The VAD may be indwelling for short term (days), moderate term (weeks), or long term (months to years).

Instrument delivery devices are often used with VADs to deliver an instrument into the indwelling intravenous (IV) catheter thereof, with the instrument delivery device advancing the instrument beyond the tip of the indwelling catheter. When the instrument delivery device is used to collect blood, as one example, the instrument can be in the form of a flexible tube or catheter, but the instrument may also be a guidewire, obturator, wire, electrical wiring, probe, or sensor(s), in other implementations. Often, when the instrument is advanced, it can encounter an obstruction, resulting in deflection of the implement. Examples of obstructions include the friction of the seal within the delivery device, torturous path within an integrated catheter, pinching of the catheter tubing as it dives into the skin, thrombus, fibrin, and valves. Further, delivery of instruments can be complicated by interchange of instruments, by the necessary length for deployment of such instruments, and by fluid leakage between the VAD and instrument delivery device. Accordingly, a need exists in the art for instrument delivery devices that allow for robust performance of the instrument that is being delivered

SUMMARY OF THE INVENTION

Provided herein is an instrument delivery device for advancing an instrument into a vascular access device. The instrument delivery device includes an outer housing defining an inner volume and having a proximal end and a distal end and a connector positioned at the distal end of the outer housing and including a projection member protruding out from the outer housing configured to mate with an access connector of the vascular access device. The instrument delivery device also includes an inner housing having a proximal end and a distal end, with the distal end positioned within the inner volume and engaged with a proximal end of the instrument, wherein the inner housing is configured to move relative to the outer housing such that a distal movement of the inner housing moves the instrument from a first position, in which a distal end of the instrument is disposed within the outer housing, to a second position, in which the distal end of the instrument is disposed beyond the distal end of the outer housing and the projection member. The instrument delivery device further includes a fluid flow preventing seal provided in or adjacent the connector and configured to prevent a transfer of fluid between the vascular access device and the inner volume of the outer housing.

In some embodiments, the fluid flow preventing seal is a flexible seal member positioned adjacent a proximal end of the connector, between the connector and the outer housing, with the flexible seal member including an opening formed therein through which the instrument passes, the opening having a diameter smaller than a diameter of the instrument, with the opening configured to stretch when the instrument is passed therethrough.

In some embodiments, a seal lubricant is applied about the opening in the flexible seal member.

In some embodiments, the fluid flow preventing seal is a fit-type seal formed between an inner diameter of a lumen formed through the projection member and an outer diameter of the instrument that that is advanced through the projection member when moved to the second position.

In some embodiments, the projection member is a blunted cannula, the blunted cannula being one of a molded plastic cannula, a metal cannula, or a metal cannula over-molded with plastic.

In some embodiments, an instrument lubricant is applied on an outer surface of the instrument, at least along a portion of the instrument that may be advanced through the fluid flow preventing seal when the instrument is moved from the first position to the second position In some embodiments, the instrument includes a base material and a low-friction coating applied on an outer surface of the base material, the low-friction coating having a lower coefficient of friction than the base material.

Also provided herein is an instrument delivery device for advancing an instrument into a vascular access device. The instrument delivery device includes an outer housing defining an inner volume and having a proximal end and a distal end and a connector positioned at the distal end of the outer housing configured to mate with an access connector of the vascular access device. The instrument delivery device also includes an inner housing having a proximal end and a distal end, with the distal end positioned within the inner volume and engaged with a proximal end of the instrument, wherein the inner housing is configured to move relative to the outer housing such that a distal movement of the inner housing moves the instrument from a first position, in which a distal end of the instrument is disposed within the outer housing, to a second position, in which the distal end of the instrument is disposed beyond the distal end of the outer housing. The instrument delivery device further includes one or more instrument supports positioned within the inner volume of the outer housing and configured to support the instrument as it is moved from the first position toward the second position, to prevent buckling of the instrument, wherein the one or more instrument supports is retained in a fixed position within the inner volume until the inner housing is moved distally into contact therewith.

In some embodiments, each of the one or more instrument supports is a support washer or a support cylinder, with an opening formed therein through which the instrument passes.

In some embodiments, each of the one or more instrument supports is retained in the fixed position within the inner volume of the housing via a friction fit or a detent feature.

In some embodiments, each of the one or more instrument supports includes a tether member affixed to an end or both ends thereof, the tether member retaining the instrument support in the fixed position within the inner volume.

In some embodiments, the inner housing slides the one or more instrument supports distally upon coming into contact therewith and continuing to move distally, and wherein the tether member is configured to return the instrument support to its original position within the inner volume, upon the inner housing being retracted proximally.

In some embodiments, a lubricant is applied to at least one of the instrument and the one or more instrument supports, to reduce friction between the instrument and the one or more instrument supports.

In some embodiments, an inner diameter of the outer housing is configured such that buckling of the instrument is limited and/or prevented when the inner housing is advanced through the outer housing.

Also provided herein is an instrument delivery device for advancing an instrument into a vascular access device. The instrument delivery device includes an inner housing having a proximal end and a distal end and a connector positioned at the distal end of the inner housing configured to mate with an access connector of the vascular access device. The instrument delivery device also includes an outer housing defining an inner volume and having a proximal end and a distal end, with the proximal end of the inner housing positioned within the inner volume of the outer housing at the distal end thereof, wherein the outer housing is configured to move relative to the inner housing such that a distal movement of the outer housing moves the instrument from a first position, in which a distal end of the instrument is disposed within the inner housing, to a second position, in which the distal end of the instrument is disposed beyond the distal end of the inner housing. In moving the outer housing distally relative to the inner housing, the outer housing is advanced over the inner housing and the inner housing is received within the inner volume of the outer housing.

In some embodiments, one or more instrument supports are positioned within the inner volume of the outer housing that are configured to support the instrument as the outer housing is moved distally over the inner housing, and as the instrument advances from the first position toward the second position, to prevent buckling of the instrument.

In some embodiments, an inner diameter of the inner housing is configured such that buckling of the instrument is limited and/or prevented when the outer housing is advanced distally over the inner housing.

Also provided herein is an instrument delivery device for advancing an instrument into a vascular access device. The instrument delivery device includes an outer housing defining an inner volume and having a proximal end and a distal end and a connector positioned at the distal end of the outer housing configured to mate with an access connector of the vascular access device. The instrument delivery device also includes an inner housing having a proximal end and a distal end, with the distal end positioned within the inner volume and engaged with a proximal end of the instrument, wherein the inner housing is configured to move relative to the outer housing such that a distal movement of the inner housing moves the instrument from a first position, in which a distal end of the instrument is disposed within the outer housing, to a second position, in which the distal end of the instrument is disposed beyond the distal end of the outer housing and into the vascular access device. The instrument delivery device further includes a first position marker provided on the inner housing adjacent the distal end thereof and a second position marker provided on the outer housing adjacent the distal end thereof, wherein the first position marker aligns with the second position marker when the instrument is in the second position, extending into the vascular access device.

In some embodiments, the first position marker is indicia arranged on a top surface of the inner housing and the second position marker is a window formed on a top surface of the outer housing, wherein the indicia is visible through the window when the instrument is in the second position.

In some embodiments, the indicia is one of a colored region, text, or a symbol.

DESCRIPTION OF THE INVENTION

Figures 1A, 1B:
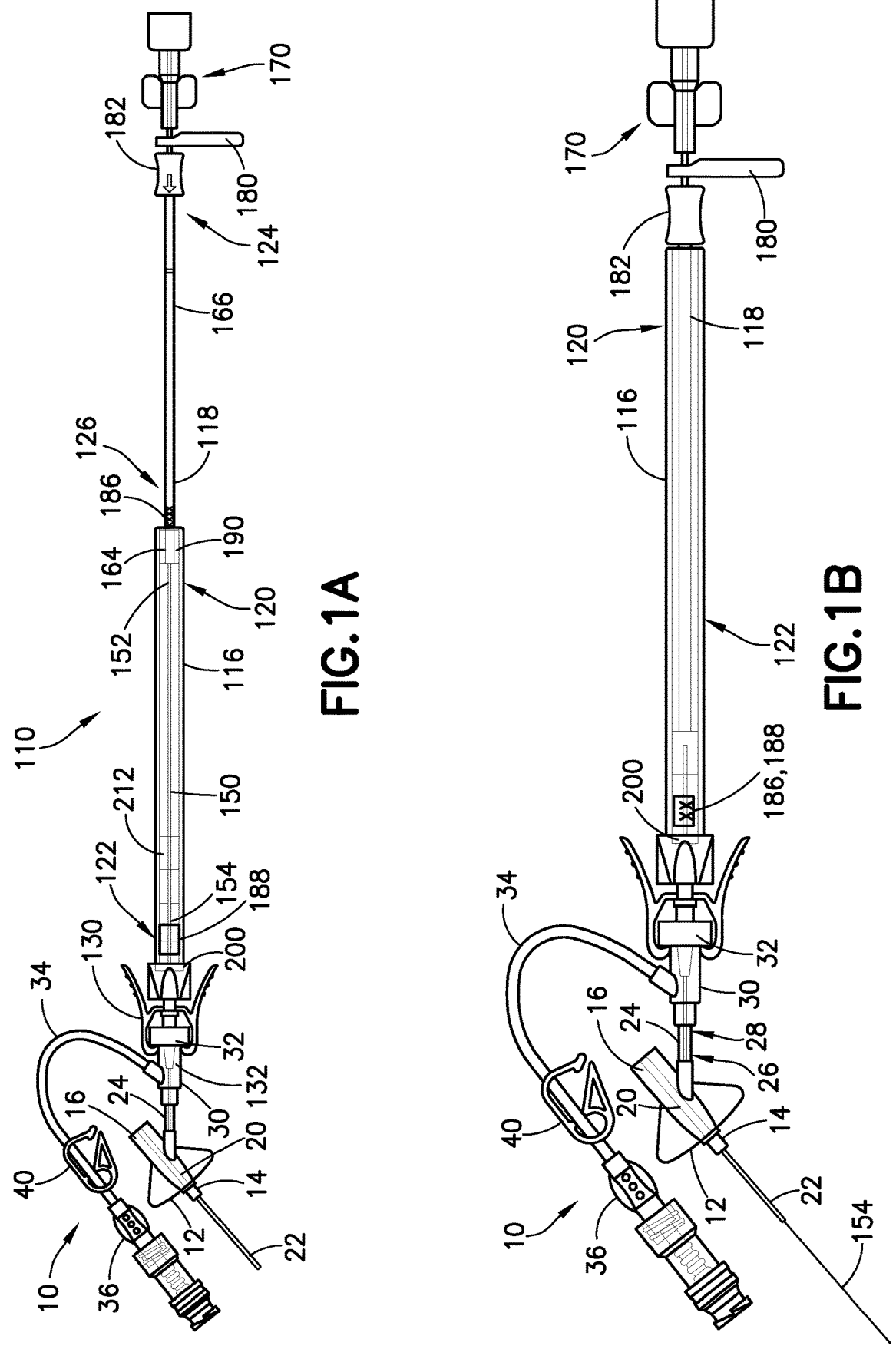
FIG. 1A shows a side view of a catheter assembly and an associated instrument delivery device useable therewith, with the instrument delivery device in a first configuration, according to a non-limiting embodiment described herein.
FIG. 1B shows a side view of the catheter assembly and associated instrument delivery device of FIG. 1A, with the instrument delivery device in a second configuration.

The following description is provided to enable those skilled in the art to make and use the described embodiments contemplated for carrying out the invention. Various modifications, equivalents, variations, and alternatives, however, will remain readily apparent to those skilled in the art. Any and all such modifications, equivalents, variations, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

As used in this specification, the words "proximal" and "distal" refer to the direction closer to and away from, respectively, a user who would place the device into contact with a patient. Thus, for example, the end of a device first touching the body of the patient would be the distal end, while the opposite end of the device being manipulated by the user would be the proximal end of the device.

The terms "first", "second", and the like are not intended to refer to any particular order or chronology, but refer to different conditions, properties, or elements.

As used herein, "at least one of" is synonymous with "one or more of." For example, the phrase "at least one of A, B, and C" means any one of A, B, or C, or any combination of any two or more of A, B, or C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C.

It should be understood that any numerical range recited herein is intended to include all values and sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value equal to or less than 10.

Provided herein are devices and systems for delivering instruments through indwelling catheters, such as peripheral intravenous catheters (PIVCs). While certain devices (e.g., blood draw devices) are discussed below in terms of devices that may be used with PIVCs, and exemplified in the attached drawings, those of skill will appreciate that any number of different devices for introducing an instrument, including instruments ranging from tubes, probes, sensors (e.g., pressure sensors, pH sensors, lactate sensors, glucose sensors, and the like), wiring, fiber optics, guidewires, etc., may be used within the scope of the present disclosure.

Referring now to FIGS. 1A and 1B, shown is a non-limiting embodiment of a system including a catheter assembly 10 and instrument delivery device 110. Suitable catheter assemblies for use with instrument delivery devices described herein are commercially available, for example from Becton, Dickinson and Company under the trade name Nexiva. Catheter assembly 10 may include a catheter adapter 12, which may include a distal end 14 and a proximal end 16. In some embodiments, the catheter adapter 12 may include one or more additional ports 18. The port 18 may be disposed between the distal end 14 and the proximal end 16, and more than one port 18 may be disposed between the distal end 14 and the proximal end 16. The port 18 may instead be disposed at proximal end 16. In some embodiments, the first catheter adapter 12 may include a first lumen 20 extending through the distal end 14 and the proximal end 16. First lumen 20 may be sealed at proximal end 16 of catheter adapter 12.

In some non-limiting embodiments or aspects, the catheter assembly 10 may include a catheter 22 extending from the distal end 14. The first catheter 22 may include a peripheral intravenous catheter, a midline catheter, or a peripherally-inserted central catheter. Catheter 22 may be formed of any suitable material and may be of any useful length, as known to those of skill in the art. In some non-limiting embodiments or aspects, the catheter assembly 10 may include a first fluid conduit 24 extending from the port 18. First fluid conduit 24 may be formed of any suitable material known to those of skill in the art, and may have a distal end 26 and a proximal end 28, and first fluid conduit 24 may be coupled, at distal end 26 thereof, to port 18. In some non-limiting embodiments or aspects, a connector 30 may be coupled to a proximal end 28 of first fluid conduit 24. Connector 30 may be a t-connector (e.g., one side port arranged at a 90 degree angle relative to a longitudinal axis of connector 30), a y-connector (e.g., one side port arranged at an angle of 15-165 degrees relative to a longitudinal axis of connector 30), or any other type of connector known in the art, and may include a second lumen therethrough, having any number of branches suitable for the type of connector.

In some non-limiting embodiments or aspects, catheter assembly 10 may include an extension set (integrated into or removably coupleable to catheter adapter 12, connector 30, and/or needleless access connector 32) including a second fluid conduit, such as second fluid conduit 34. Extension sets are known to those of skill in the art and are commercially available from, for example, Becton, Dickinson and Company. In some non-limiting embodiments or aspects, second fluid conduit 34 may include a luer connection 36 at an end thereof. The extension set may also include a clamp 40, to allow for occlusion of second fluid conduit 34. Clamp 40 and second fluid conduit 34 may be formed of any suitable materials known to those of skill in the art. In non-limiting embodiments, second lumen (e.g., within connector 30) has an inner diameter that is substantially equivalent to an inner diameter of first fluid conduit 24 and/or second fluid conduit 34.

Catheter assembly 10 may include a needleless access connector 32 and/or a second fluid conduit 34. Suitable needleless access connectors 32 can include any split-septum connector and/or those with direct fluid path access. Needleless access connectors 32 are known to those of skill in the art and are commercially available from, for example, Becton, Dickinson and Company under the trade names Q-SYTE and SMARTSITE. While the non-limiting embodiments of FIGS. 1A and 1B show needleless access connectors arranged at connector 30, those of skill in the art will appreciate that suitable needleless access connectors may also be arranged at luer 36. In non-limiting embodiments, needleless access connector 32 includes a septum (not shown), such as a slit-type, self-healing septum. As will be described below, instrument delivery device 110 may be reversibly coupleable to the needleless access connector 32, and one or more portions of the instrument delivery device may pierce the septum and access the patient's vasculature through catheter 22.

Figure 2:
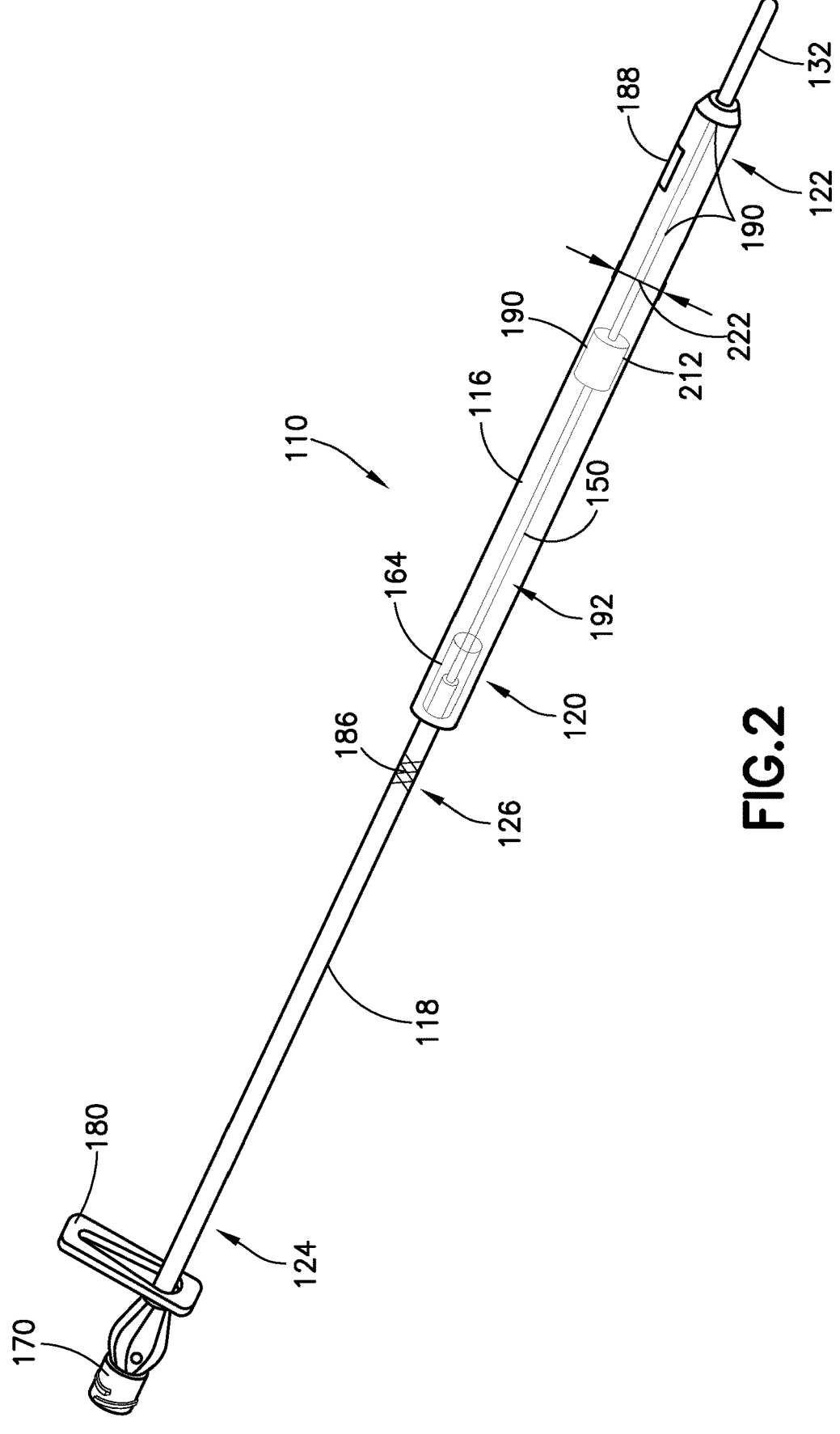
FIG. 2 shows a perspective view of the instrument delivery device of FIGS. 1A and 1B.

With continuing reference to FIGS. 1A and 1B and now also to FIG. 2, instrument delivery device 110 includes an outer housing 116 having a proximal end 120 and a distal end 122, and an inner housing 118 slideably received within outer housing 116. In non-limiting embodiments, inner housing 118 and outer housing 116 are in a telescoping relationship, such that inner housing 118 may be slideably received entirely, or almost entirely, within outer housing 116. Inner housing 118 also includes a proximal end 124 and a distal end 126 and, in non-limiting embodiments, inner housing may have a variable diameter along its length. As one example, the distal end 126 of inner housing 118 may have a larger diameter than other portions of inner housing 118, to provide more local stiffness or a sliding feature(s) to limit friction or binding. As another example, the distal end 126 of inner housing 118 may have a smaller diameter than other portions of inner housing 118, to position to keep the inner housing 118 in position at a blood draw forward condition, so that a hand of the operator is freed up to manipulate additional components (e.g., a vacutainer tube). Instrument delivery device 110 further includes an instrument 150 having a proximal end 152 and a distal end 154.

While instrument 150 is exemplified in the drawings as a catheter or fluid conduit, those of skill in the art will appreciate that the instrument 150 may be any medical instrument that can be delivered through catheter assembly 10 to a patient's vasculature, such as a guidewire, obturator, wire, electrical wiring, probe, sensor, or the like.

Instrument 150 is received within outer housing 116, and may be advanced and/or retracted relative to outer housing 116 by displacement of the inner housing 118 relative to the outer housing 116. In non-limiting embodiments, instrument 150 may be advanced from a first positon as shown in FIG. 1A, in which distal end 154 of instrument 150 is within instrument delivery device 110, for example within outer housing 116 and/or a connector 130 (that secures instrument delivery device 110 to needleless access connector 32, for example), to a second position as shown in FIG. 1B, in which a distal end 154 of instrument 150 is positioned distally of connector 130 and, in embodiments in which instrument delivery device 110 is coupled to catheter assembly 10, optionally distally of catheter 22. While connector 130 is exemplified as a lock (hereafter "lock 130") that includes a blunt cannula 132 and arms 134, those of skill will appreciate that any type of suitable connection may be used to secure instrument delivery device 110 to an indwelling catheter, such as catheter assembly 10, including luer connections, clips, blunt plastic cannulae, blunt metal cannulae, hybrid luers (e.g., with a cannula) friction fits, and the like.

Instruments 150 useful with the instrument delivery device 110 described herein may be formed of any useful material. In non-limiting embodiments, instrument 150 is a fluid conduit, which is formed of a polymer, such a polyimide-containing material, nylon, polyurethane, and other suitable polymeric material. In other embodiments, the instrument 150 includes a base material and a low-friction coating applied on an outer surface of the base material, the low-friction coating having a lower coefficient of friction than the base material. In addition, inner housing 118 may be formed of any suitable material, including polymeric materials, elastomeric materials, metallic materials, and combinations thereof, so long as the material is sufficiently rigid so as to reduce buckling. In non-limiting embodiments, inner housing 118 is formed of a material that provides resistance to buckling, such as polyethylene, polypropylene, nylon, polyurethane, and the like.

As can be appreciated, FIG. 1A shows instrument delivery device in a first state, where instrument 150 is in a first position, received within outer housing 116, and inner housing 118 is in a first position, extending proximally from outer housing. In non-limiting embodiments, inner housing 118 is coupled to or otherwise interacts with instrument 150, such that as inner housing 118 is advanced distally to a second position, as shown in FIG. 1B, instrument 150 is moved to a second position, where a distal end 154 of instrument 150 extends beyond outer housing 116, lock 130 (if present), and/or catheter 22.

In non-limiting embodiments, the inner housing 118 may be advanced distally relative to the outer housing 116 by way of a user grasping grip 182 and applying a distally-directed force to inner housing 118. Grip 182 may be arranged at a proximal end of inner housing 118, and may be arranged at or near a clamp 180 suitable for occluding fluid flow through inner housing 118 and/or instrument 150, as will be described in greater detail below. Grip 182 may be formed of an ergonomic material, to provide comfort while a user grips the instrument delivery device 110, and may include features to, for example, increase grip and prevent slippage while inner housing 118 is being advanced/retracted.

As described above, a distal end of inner housing 118 may be of a larger diameter than other portions of inner housing 118, such that, as inner housing 118 is retracted, one or more features on outer housing 116 may interact with the enlarged portion of inner housing 118 to prevent pulling inner housing 118 completely out of outer housing 116. Enlarged distal portion of inner housing 118 may include vents for allowing air to pass therethrough, reducing force needed to advance/retract inner housing 118, and, as described below, lubricant 190 may be applied to an enlarged portion of inner housing 118 to reduce friction between inner housing 118 and outer housing 116.

Inner housing 118 may include, at the proximal end 124 thereof, a connector 170, to allow for various medical devices to be attached to inner housing 118, for example to provide an instrument that is to be advanced into the patient's vasculature, to inject a composition into the vasculature, and/or to receive fluid withdrawn from the vasculature. Suitable connectors 170 include luer connectors, luer lock access devices, needless access connectors, electrical connectors, optical connectors, and the like known to those of skill in the art, including any combination of the aforementioned connector types.

In non-limiting embodiments where instrument 150 is a fluid conduit, fluid (e.g., blood) may be transferred into or from the patient's vasculature in which a catheter, such as catheter 22, may be indwelling. As shown in FIGS. 1A and 1B and FIG. 2, the fluid conduit 150 may be joined at fitting 164 to inner housing 118. According to non-limiting embodiments, fluid conduit 150 may be joined at fitting 164 to a separate fluid tube 166 that passes through inner housing 118 and is coupled to connector 170. In other non-limiting embodiments, fluid conduit 150 may be joined at fitting 164 to inner housing 118, with inner housing 118 itself forming a fluid conduit in fluid communication with connector 170 (i.e., inner housing 118 acts as a fluid conduit, in lieu of a separate fluid tube 166). In either of the above described embodiments, a fluid control component 180 may be provided at the proximal end 124 of inner housing 118 that is suitable for occluding fluid flow through inner housing 118 and/or fluid conduit 150. While fluid control component 180 is illustrated as a clamp (e.g., a slide clamp or a pinch clamp), the component 180 may instead be a valve (e.g., stopcock), according to embodiments.

In non-limiting embodiments inner housing 118 and outer housing 116 may include position markers 186, 188 to indicate instrument length and instrument positioning relative to the indwelling catheter 22. In non-limiting embodiments, a first position marker 186 on the inner housing 118 may be provided as indicia 186, such as a colored region, text, or a symbol, and a second position marker 188 may be provided on the outer housing 116 as a window 188 formed of material that is at least partially transparent. The indicia 186 may be provided on a top surface (or about an entire outer surface) of the inner housing 118 adjacent the distal end 126 thereof, and the window 188 may similarly be provided on a top surface of the outer housing 116 adjacent the distal end 122 thereof. The indicia 186 and window 188 allow an operator to identify the positioning of the inner housing 118 relative to the outer housing 116 and, in turn, the positioning of the instrument 150. In particular, the indicia 186 and window 188 allow an operator to identify when the instrument 150 is in the second position, with the instrument 150 extending into the catheter assembly 10 and into or past the indwelling catheter 22 thereof. With the instrument 150 in the second position, the inner housing 118 is advanced into the outer housing 116 such that the indicia 186 is aligned with the window 188 and is visible there-through. With indicia 186 being visible within window 188, an operator is reminded that the instrument 150 is fully advanced and needs to be retracted back toward the first position before the instrument delivery device 110 can be removed from the catheter assembly 10.

While position markers 186, 188 are described above as indicia 186 and window 188, additional embodiments may include second position marker 188 being in the form of additional indicia provided on a top surface of the outer housing 116. In such an embodiment, a top surface of the outer housing 116 may be formed of material that is at least partially transparent, along a length of the outer housing 116 to allow for visualization of indicia 186 throughout the transition from a first positon of inner housing 118 to a second position of inner housing 118. The additional indicia may be provided below this transparent material at the distal end 122 of the outer housing. When the inner housing 118 is advanced into the outer housing 116 to move the instrument 150 into the second position, the indicia 186 on inner housing 118 will align with the additional indicia on outer housing 116 (with both visible through the transparent top surface of outer housing 116), to indicate to an operator the instrument 150 is fully advanced and needs to be retracted back toward the first position before the instrument delivery device 110 can be removed from the catheter assembly 10.

According to embodiments, instrument delivery device 110 may include any of a number of features that prevent unwanted fluid transfer between the catheter assembly 10 and the instrument delivery device 110—such as preventing blood or other fluids from leaking out of or entering the blood stream other than through the intended ports. That is, various fluid flow preventing seals may be provided in or adjacent the lock 130 of instrument delivery device 110 that are configured to prevent an unwanted transfer of fluid between the catheter assembly 10 and an inner volume 192 (FIG. 2) of the outer housing 116.

Figures 3, 4:
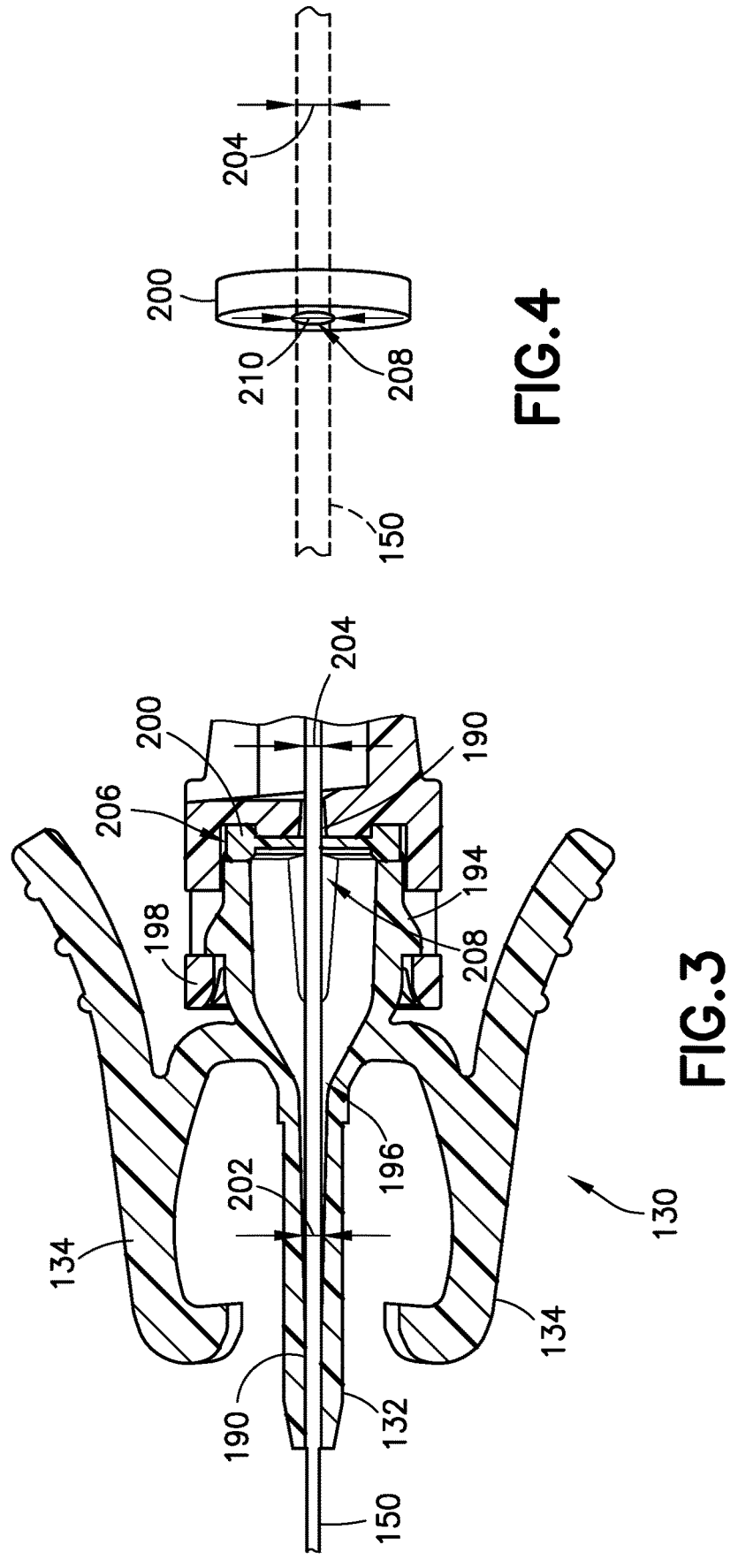
FIG. 3 shows a partial cross-section view of the instrument delivery device of FIG. 1A, taken along line a-a, illustrating a connector, according to an embodiment described herein.
FIG. 4 shows an isolated view of a seal member included in the connector of FIG. 3.

With continuing reference to FIGS. 1A and 1B, and now to FIG. 3, the lock 130 of the instrument delivery device 110 is configured to be physically and fluidically coupled to the outer housing 116 and configured to couple the instrument delivery device 110 to an access device of the catheter assembly 10, such as needleless access connector 32. The lock 130 has a coupler 194, a blunt cannula 132, and a pair of arms 134, as shown in FIG. 3. In addition, the lock 130 defines a lumen 196 extending through the coupler 194 and the blunt cannula 132, The coupler 194 is configured to couple the lock 130 to an end coupler 198 of the outer housing 116. Specifically, in this embodiment, the coupler 194 includes and/or forms one or more protrusions config-ured to selectively engage threads defined and/or formed in the end coupler 198 of the outer housing 116, thereby forming a threaded coupling.

The blunt cannula 132 extends from the coupler 194 and is disposed between the pair of arms 134. The blunt cannula 132 can be any suitable construction, shape, size, and/or configuration. In some embodiments, the blunted cannula 132 may be constructed as a molded plastic cannula, a metal cannula, or a metal cannula over-molded with plastic, with the lumen 196 thus defined by a molded plastic cannula or a metal cannula (itself or over molded with plastic). The blunt cannula 132 can have a length that is sufficient to extend through at least the needleless access connector 32 and into connector 30 of catheter assembly 10. In embodi-ments, the size tolerance of the lumen 196 may be tightly controlled when manufacturing the lock 130/cannula 132, it order to control a gap between the outer surface of the instrument 150 and the inner surface of the lumen 196, as described further below.

In some embodiments, a fluid flow preventing seal is formed within the lock 130 based on a sizing of the lumen 196 in blunted cannula 132 relative to a sizing of the instrument 150. That is, the lumen 196 can have an inner diameter 202 (i.e., a diameter of a surface at least partially defining the lumen 196) that is similar to or slightly larger than an outer diameter 204 of a portion of the instrument 150—e.g., within 0.5 mm—such that a fit-type seal is formed between the inner diameter 202 of lumen 196 within blunted cannula 132 and the outer diameter 204 of the instrument 150 as the instrument is advanced through the blunted cannula 132 when the instrument is moved to the second position. By minimizing the space between the inner diameter 202 of lumen 196 and the outer diameter 204 of the instrument 150, the space within which fluid can flow therebetween is reduced, thereby slowing or stopping any such fluid flow if the space is small enough to balance the pressure and surface tension of the fluid.

In some embodiments, a lubricant 190 (e.g., silicone-based lubricant) can be added to the lumen 196 of blunted cannula 132 or to the outer surface of instrument 150 to reduce friction between the instrument 150 and the blunted cannula 132. In addition to reducing friction, the lubricant 190 can also fill any remaining gap between the inner diameter 202 of lumen 196 and the outer diameter 204 of the instrument 150 to further aid in preventing fluid flow through this gap.

In some embodiments, a fluid flow preventing seal is formed adjacent the lock 130 via providing of a flexible septa or seal member 200. The flexible seal member 200 is positioned adjacent a proximal end of the lock 130, such as between the coupler 194 and the end coupler 198 of outer housing 116, and may be seating in a groove 206 formed in the end coupler 198 to be retained in place upon coupler 194 being coupled thereto (e.g., via a threaded engagement or snap-fit). The flexible seal member 200 may be formed of a flexible, elastomeric material according to one embodiment, and includes an opening 208 formed therein through which the instrument 150 passes. As shown in FIG. 4, the opening 208 has a diameter 210 smaller than the outer diameter 204 of the instrument 150, with the opening 208 configured to stretch when the instrument 150 is passed therethrough. Based on the sizing of the opening, a seal is formed between the seal member 200 and the instrument 150 as the instru-ment is advanced through the opening when the conduit is moved to the second position. In some embodiments, a lubricant 190 (e.g., silicone-based lubricant) can be added to the opening 208 of seal member 200 or to the outer surface of instrument 150 to reduce friction between the instrument 150 and the seal member 200.

According to embodiments, instrument delivery device 110 may also include any of a number of features that provide a more robust system for accessing a patient's vasculature—such as limiting and/or preventing bowing and buckling of the instrument 150. That is, various support, restraint and guidance features may be provided in the instrument delivery device 110 that function to minimized bowing and buckling of the instrument 150 as it is advanced through the outer housing 116.

Figure 5:
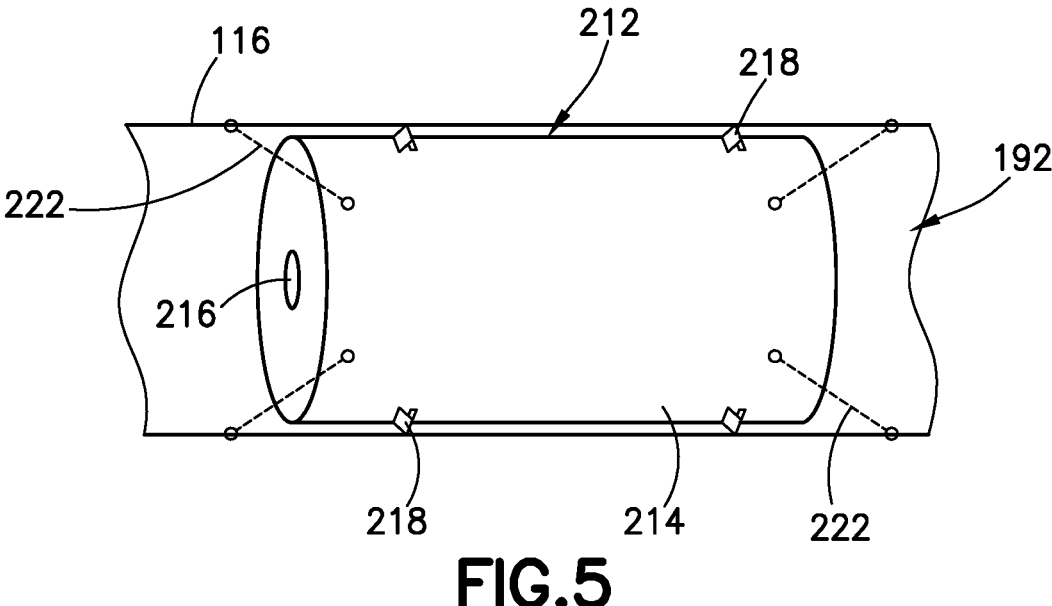
FIG. 5 shows an isolated view of an instrument support included in the instrument delivery device of FIG. 1A, according to an embodiment described herein.
Figure 6:
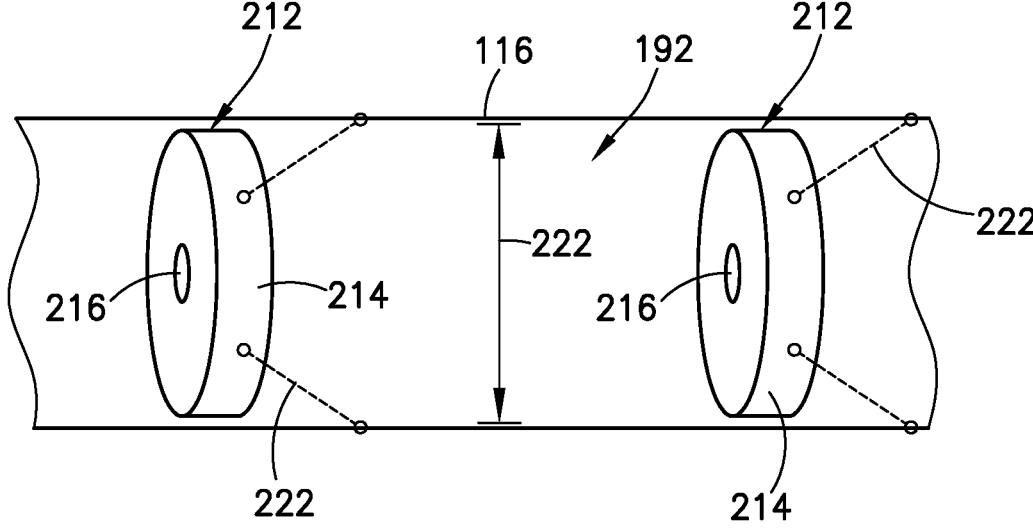
FIG. 6 shows an isolated view of an instrument support included in the instrument delivery device of FIG. 1A, according to another embodiment described herein.

As shown in FIGS. 1A, 1B and 2, and now in FIGS. 5 and 6, instrument delivery device 110 includes one or more instrument supports 212 arranged within the inner volume 192 of outer housing 116, to limit and/or prevent buckling of the instrument 150 as inner housing 118 and/or the instrument 150 are advanced distally through outer housing 116. In some embodiments, multiple instrument supports 212 are provided and positioned at optimal locations between the proximal and distal ends 120, 122 of the outer housing 116 that are determined to provide the necessary support to the instrument 150 as it is advancement distally by instrument delivery device 110, such as at locations where the instrument 150 encounters the greatest drag and/or resistance. The instrument supports 212 effectively break the single long column of the instrument 150 into multiple shorter columns, each of which has a much higher buckle strength than the single long column.

As shown in the embodiments of FIGS. 5 and 6, each of the instrument supports 212 has a body 214 that, according to embodiments, may be configured as a washer or cylindrical shaped structure, or may have another cross-sectional shape that is based at least in part on a cross-sectional shape of the outer housing 116. The body 214 defines a passageway 216 that is sized and shaped to allow the instrument 150 to freely pass therethrough, while being at least partially contained to prevent excessive movement of the instrument 150 within the inner volume 192 of the outer housing 116.

According to embodiments, the body 214 of each of the instrument supports 212 may be sized and/or include features thereon that help to retain the instrument support 212 in place within the outer housing 116. In one embodiment, the outer diameter of the body 214 of instrument support 212 is close to the inner diameter of the outer housing 116, such that a friction fit is provided between the instrument support 212 and the outer housing 116 to retain the instrument support 212 in place. In another embodiment, the body 214 of instrument support includes detents 218 formed on an outer surface thereof that interact with the inner surface of outer housing 116 to retain the instrument support 212 in place. Via one of these features described above, the instrument supports 212 may be retained in place within the outer housing 166 until operation of the instrument delivery device 110 causes inner housing 118 to move distally within outer housing 116 and come into contact with the instrument support 212. Upon coming into contact with the instrument support 212 and continuing to move in the distal direction, the inner housing 118 causes the one or more instrument supports 212 to slide distally within the outer housing 116.

In some embodiments, each of the body of instrument supports 212 may have one or more tether members 220 secured to the body and extending between the body 214 and the outer housing 116. The tether members 220 may be configured as flexible, stiff, or semi-stiff members. Each instrument support 210 may have a single tether member 220 coupled to one end of the body 214, or two tether members 220 coupled to opposing ends of the body 214, according to embodiments. The tether members 220 function to return the instrument support 212 to its original position within the inner volume 192 (i.e., reset the position of the instrument support 212) after the inner housing 118 has caused the instrument support 212 to slide distally within the outer housing 116, with the tether members 220 pulling the instrument support 212 back to its original position upon the inner housing 118 being retracted back toward the proximal end 120 of outer housing 116.

To further reduce the chances for bowing or buckling of the instrument 150 to occur, friction reducing materials or coatings may be utilized on various components of the instrument delivery device 110. In some embodiments, various components of the instrument delivery device 110, such as the instrument 150, instrument supports 212, seals 200, lock 130 (or portions thereof), etc., may be formed of low friction materials, such as polyethylene, polypropylene, or PTFE, as examples. In other embodiments, one or more of the above components may have a low-friction coating applied on an outer surface of the base material of the component, with the low-friction coating having a lower coefficient of friction than the base material. The coating may be provided as PTFE or parylene, as examples. In still other embodiments, an appropriate lubricant 190 (e.g., silicone oil) may be applied to one or more of the above components. All of these will reduce friction and aid in the advancement and insertion of the instrument 150.

In some embodiments, the outer housing 116 may be configured to limit the amount of bowing and buckling experienced by the instrument 150 as it is advanced through the outer housing 116. To reduce the amount by which the instrument 150 may bow or buckle during advancement, an inner diameter 222 of the outer housing 116 may be reduced so as to reduce the available space within which the instrument 150 may deflect as it is advanced, thereby controlling the shape and amount by which the instrument 150 bows. When the instrument 150 starts to bow under compressive forces, it will contact the small internal diameter 222 of the outer housing 116, thereby preventing it from further bowing or buckling.

Figures 7A, 7B:
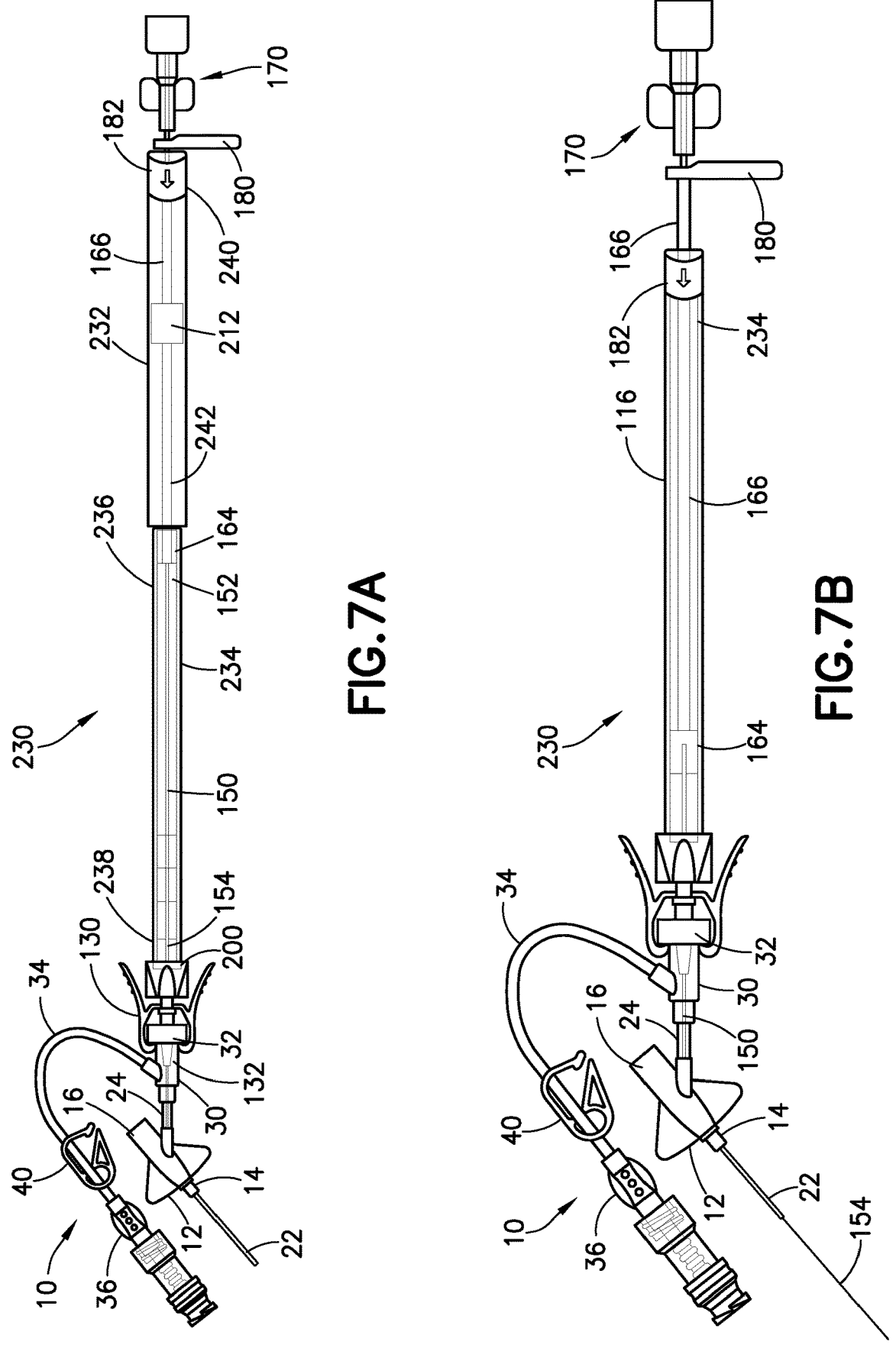
FIG. 7A shows a side view of a catheter assembly and an associated instrument delivery device useable therewith, with the instrument delivery device in a first configuration, according to another non-limiting embodiment described herein.
FIG. 7B shows a side view of the catheter assembly and associated instrument delivery device of FIG. 7A, with the instrument delivery device in a second configuration.
Figure 8:
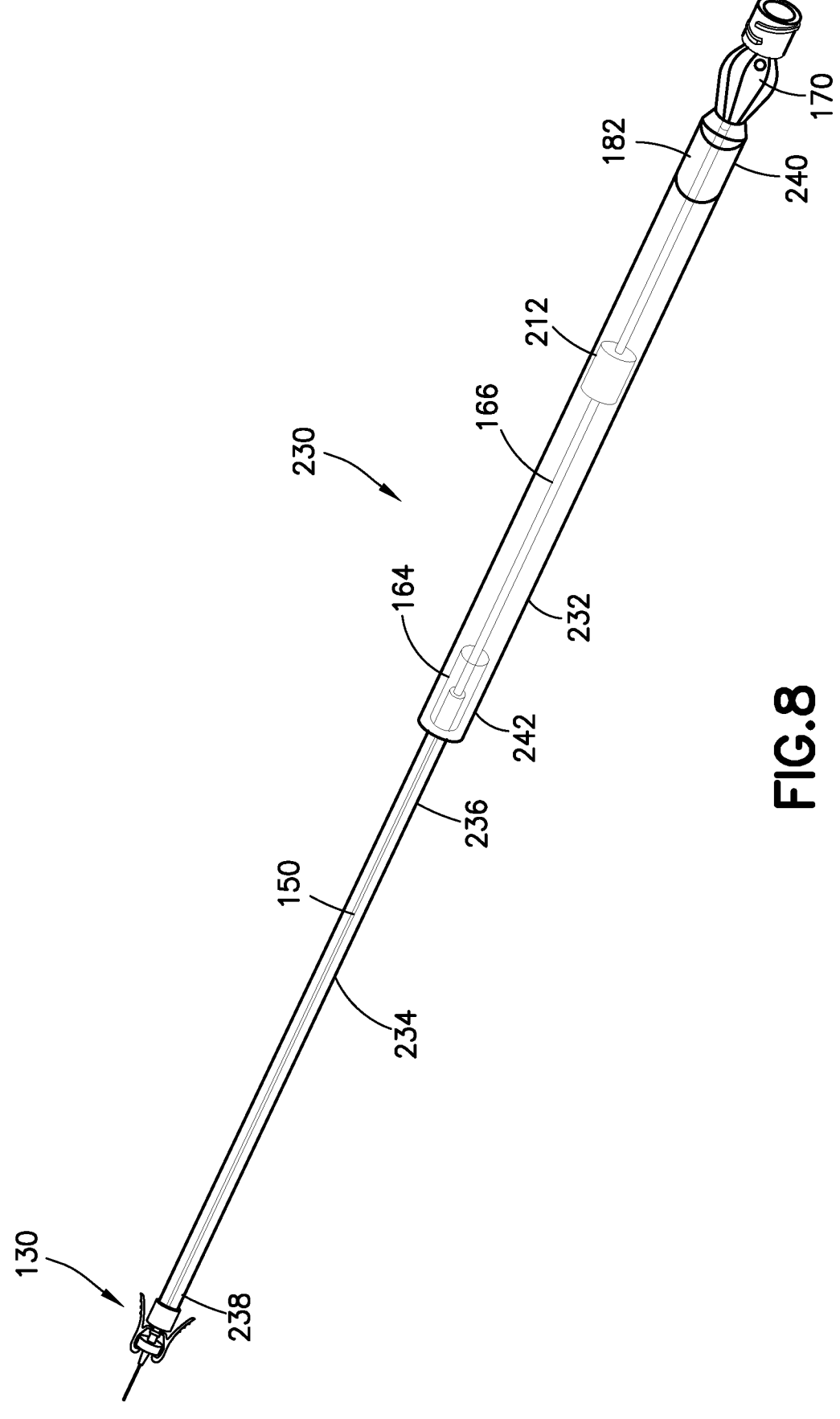
FIG. 8 shows a perspective view of the instrument delivery device of FIGS. 7A and 7B.

Referring now to FIGS. 7A, 7B and 8, an instrument delivery device 230 is shown according to another embodiment. The instrument delivery device 230 may generally be described as a "reverse nested housing" device, as it includes an outer housing 232 and an inner housing 234 in a telescoping relationship, but in a reversed arrangement as compared to the inner housing 118 and outer housing 116 of instrument delivery device 110—i.e., inner housing 234 is positioned distally and adjacent to a catheter assembly 10 that is connected thereto, while outer housing 232 is positioned proximally away from the catheter assembly 10. The inner housing 234 includes a proximal end 236 and a distal end 238 and the outer housing 232 includes a proximal end 240 and a distal end 242. The outer housing 232 may be advanced distally via interaction therewith by an operator, such that the outer housing 232 slides over the inner housing 234 and such that the inner housing 234 is received entirely, or almost entirely, within outer housing 232.

Instrument delivery device 230 further includes an instrument 150 exemplified in the drawings as a catheter or fluid conduit having a proximal end 152 and a distal end 154, but, as described previously and as will be appreciated by those of skill in the art, may be any medical instrument that can be delivered through catheter assembly 10 to a patient's vasculature. In embodiments where instrument 150 is a fluid conduit, the fluid conduit may be joined at fitting 164 to a separate fluid tube 166 that passes through outer housing 232 and is coupled to connector 170.

Instrument 150 is received within inner housing 234, and may be advanced and/or retracted relative to inner housing 234 by displacement of the outer housing 232 relative to the inner housing 234. In non-limiting embodiments, instrument 150 may be advanced from a first positon as shown in FIG. 7A, in which distal end 154 of instrument 150 is within instrument delivery device 230, for example within inner housing 234 and/or a lock 130 (that secures instrument delivery device 230 to needleless access connector 32, for example), to a second position as shown in FIG. 7B, in which a distal end 154 of instrument 150 is positioned distally of connector 130 and, in embodiments in which instrument delivery device 230 is coupled to catheter assembly 10, optionally distally of catheter 22.

In some embodiments, the outer housing 232 may be advanced distally relative to the inner housing 234 by way of a user grasping grip 182 and applying a distally-directed force to outer housing 232. Grip 182 may be arranged at the proximal end 240 of outer housing 232 and may be formed of an ergonomic material, to provide comfort while a user grips the instrument delivery device 230, and may include features to, for example, increase grip and prevent slippage while outer housing 232 is being advanced/retracted.

By positioning the smaller diameter inner housing 234 closer to the catheter assembly 10 and patient, the inner housing 234 is able to limit the amount of bowing and buckling experienced by the instrument 150 as it is advanced through the inner housing 234. That is, as the inner housing 234 has a smaller inner diameter than the outer housing 232, the inner housing 234 reduces the available space within which the instrument 150 may deflect as it is advanced, thereby controlling the shape and amount by which the instrument 150 bows. When the instrument 150 starts to bow under compressive forces, it will contact the small internal diameter of the inner housing 234, thereby preventing it from further bowing or buckling.

In some embodiments, one or more instrument supports 212 may be arranged within outer housing 232, to limit and/or prevent buckling of the instrument 150 as the instrument is advanced distally through inner housing 234 (responsive to distal movement of outer housing 232). In some embodiments, multiple instrument supports 212 are provided and positioned at optimal locations between the proximal and distal ends 240, 242 of the outer housing 232 that are determined to provide the necessary support to the instrument 150 as it is advancement distally by instrument delivery device 230, such as at locations where the instrument 150 encounters the greatest drag and/or resistance. The instrument supports 212 effectively break the single long column of the instrument 150 into multiple shorter columns, each of which has a much higher buckle strength than the single long column.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. An instrument delivery device for advancing an instrument into a vascular access device, the instrument delivery device comprising:
   an outer housing defining an inner volume and having a proximal end and a distal end;
   a connector positioned at the distal end of the outer housing and comprising a projection member protruding out from the outer housing configured to mate with an access connector of the vascular access device;
   an inner housing having a proximal end and a distal end, with the distal end positioned within the inner volume and engaged with a proximal end of the instrument, wherein the inner housing is configured to move relative to the outer housing such that a distal movement of the inner housing moves the instrument from a first position, in which a distal end of the instrument is disposed within the outer housing, to a second position, in which the distal end of the instrument is disposed beyond the distal end of the outer housing and the projection member; and
   a fluid flow preventing seal provided in or adjacent the connector and configured to prevent a transfer of fluid between the vascular access device and the inner volume of the outer housing,
   wherein the inner housing is slideably received within the outer housing in a telescoping relationship.

2. The instrument delivery device of claim 1, wherein the fluid flow preventing seal comprises a flexible seal member positioned adjacent a proximal end of the connector, between the connector and the outer housing, with the flexible seal member including an opening formed therein through which the instrument passes, the opening having a diameter smaller than a diameter of the instrument, with opening configured to stretch when the instrument is passed therethrough.

3. The instrument delivery device of claim 2, further comprising a seal lubricant applied about the opening in the flexible seal member.

4. The instrument delivery device of claim 1, wherein the fluid flow preventing seal comprises a fit-type seal formed between an inner diameter of a lumen formed through the projection member and an outer diameter of the instrument that is advanced through the projection member when moved to the second position.

5. The instrument delivery device of claim 1, wherein the projection member comprises a blunted cannula, the blunted cannula being one of a molded plastic cannula, a metal cannula, or a metal cannula over-molded with plastic.

6. The instrument delivery device of claim 1, further comprising an instrument lubricant applied on an outer surface of the instrument, at least along a portion of the instrument that may be advanced through the fluid flow preventing seal when the instrument is moved from the first position to the second position.

7. The instrument delivery device of claim 1, wherein the instrument comprises a base material and a low-friction coating applied on an outer surface of the base material, the low-friction coating having a lower coefficient of friction than the base material.

* * * * *